United States Patent [19]

Matsushita et al.

[11] Patent Number: 4,556,538

[45] Date of Patent: Dec. 3, 1985

[54] CHROMATOGRAPHIC APPARATUS

[75] Inventors: Susumu Matsushita, Shinnanyo; Yoshimitsu Tada, Tokuyama; Tetsuo Ikushige, Yamaguchi; Nobuyuki Baba, Atsugi, all of Japan

[73] Assignee: Toyo Soda Manufacturing Co., Inc., Japan

[21] Appl. No.: 361,423

[22] Filed: Mar. 24, 1982

[30] Foreign Application Priority Data

Mar. 27, 1981 [JP] Japan .................................. 56-44094

[51] Int. Cl.[4] .......................................... G01N 31/08
[52] U.S. Cl. ..................................................... 422/70
[58] Field of Search .......................... 422/70; 436/161; 73/61.1 C; 222/55

[56] References Cited

U.S. PATENT DOCUMENTS

| | | | |
|---|---|---|---|
| 3,522,725 | 8/1970 | Waters | 422/70 |
| 3,855,129 | 12/1974 | Abrahams et al. | 422/70 |
| 4,047,892 | 9/1977 | Fuller | 436/161 |
| 4,191,649 | 3/1980 | Hartwick | 73/61.1 C |
| 4,199,323 | 4/1980 | Miller et al. | 436/161 |
| 4,265,634 | 5/1981 | Pohl | 436/161 |

*Primary Examiner*—Hiram H. Bernstein
*Attorney, Agent, or Firm*—Wyatt, Gerber Shoup, Scobey and Badie

[57] ABSTRACT

The present invention relates to a chromatographic apparatus for analyzing a sample of an aqueous solution containing a plurality of micro-concentration components. In the apparatus an aqueous solution sample and an eluting solution are introduced into a separating column having a length of 20 to 90 mm, which is filled with a predetermined separating carrier and placed in a thermostatic oven which also contains a detecting cell connected to the separating column, by means of a constant flow, pulse free feeding pump.

1 Claim, 4 Drawing Figures

CHROMATOGRAPHIC APPARATUS

BACKGROUND OF THE INVENTION (1) Field of the Invention

The present invention relates to a chromatographic method and apparatus for analyzing samples in aqueous solutions containing a plurality of micro-concentration components.

(2) Description of the Prior Art

As the early analytic apparatus of this type, there can be mentioned an amino acid analysis apparatus developed by W. H. Stein and F. Moore in 1951. Then, with development of the high speed liquid chromatographic technique, there have been proposed various analytic apparatuses.

In deionization or ion exchange chromatography, highly ionized samples are separated using an ion exchange resin, and they are quantitatively detected by using, for example, a conductimetric cell.

The system of this type was first developed by Wickbolt [see Z. Anal. Chem., 132, 401 (1951)]. However, in this system, a liquid feed pump is not used and the efficiency of a packed column is low. Accordingly, this apparatus requires a very long time for the analysis and the sensitivity is low.

In the ion chromatograph subsequently developed by Hamish Small, Timothy S. Stevens and William C. Bauman [see Anal. Chem., 47, 1801 (1975)], a high-speed liquid chromatographic technique is utilized and a separating column packed with a pellicular ion exchange gel and a deionizing column are used, whereby high-sensitivity analysis of various ions can be attained.

Ion exchange chromatographs heretofore developed are defective in that the efficiency of separation of ions from one another is low and since the independent liquid feed pump and various connecting members are necessary for regeneration of the deionizing column, the size of the apparatus is inevitably increased and the structure is inevitably complicated.

D. T. Gjerde and J. S. Fritz proposed a method in which the deionizing column is removed from the apparatus of Hamish Small et al. and the remaining system is combined with a large column packed with a wholly porous ion exchange gel, whereby the apparatus is simplified to some extent [J. Chromatogr., 176, 199 (1979)]. According to this proposal, however, the apparatus is still large. Additionally, it has been confirmed that this method is inferior to the above-mentioned method of Hamish Small et al. in the sensitivity.

As will be apparent from the foregoing description, no satisfactory method or apparatus for analyzing a plurality of micro-concentration components present in an aqueous solution has yet been developed, and development of a chromatographic analysis method and apparatus capable of performing analyses at a high efficiency with ease has not yet been achieved.

SUMMARY OF THE INVENTION

One object of the invention is to eliminate the foregoing defects of conventional techniques. It is a primary object of the present invention to provide a chromatographic analytic method and apparatus by which a plurality of micro-concentration components present in an aqueous solution can be separated promptly and simultaneously with a good reproducibility.

In accordance with one aspect of the present invention, there is provided a chromatographic analytic method which comprises introducing a sample of an aqueous solution containing a plurality of micro-concentration components and an eluting solution into a separating column having a length of 20 to 90 mm. The column filled with a separating carrier and placed in a thermostatic oven which also contains a detecting cell connected to the separating column, by means of a constant flow, pulse free feeding pump through a sample introduction device connected to the thermostatic oven.

In accordance with another aspect of the present invention, there is provided a chromatographic analytic apparatus which comprises a column for separating a sample of an aqueous solution introduced from a sample introduction device, a detector for detecting eluates from the separating column and a pump for feeding an eluting solution to the separating column, wherein a separating column having a length of 20 to 90 mm, which is filled with a separating carrier, and a detecting cell for detecting eluates from the separating column are arranged in a thermostatic oven in association with a constant flow, pulse free feeding pump used as the pump for feeding the eluting solution to the separating column.

The separating column used in the present invention is employed to separate a plurality of micro-concentration components present in an aqueous solution at high efficiency. The inner diameter of the column is ordinarily in the range of 2 to 20 mm, and a pressure-resistant cylindrical column composed of stainless steel, Teflon, acrylic resin, polyethylene or glass is used. If the length of the separating column exceeds 90 mm, the volume of eluting fluid which is not used for the separation is increased and the separation efficiency is reduced, and furthermore, the size of the apparatus is increased. If the length of the column is less than 20 mm, fabrication of the column becomes difficult.

A separating carrier capable of separating a plurality of micro-concentration components present in an aqueous solution promptly and simultaneously with a good chromatographic reproducibility is used as the separating carrier to be packed in the separating column. Ion exchange gels containing a sulfonic acid, trimethyl ammonium group or amino groups are especially preferred. These gels satisfy the following requirements: (a) the particles size is 1 to 8 $\mu$m and the gel has spherical shape, (b) the gel is porous and has a pore size smaller than 1000 Å, (c) the exchange capacity is 0.03 to 1.0 milliequivalent/g, and (d) the gel has a mechanical strength characterized by a compression strength of at least 200 Kg/cm$^2$.

The detecting cell is arranged to detect a plurality of micro-concentration components separated by the separating column without reduction in separation efficiency. It is preferred to use small-capacity cells which do not cause disturbance of the components separated by the separating column or substantially reduce the separation efficiency. Cells having a capacity less than 1.9 $\mu$l are preferred. Suitable detectors include fluorescent, conductivity, dielectric constant, electrochemical and utlraviolet detectors, and these are normally selected based on the kinds of components to be detected.

In order to separate the respective components with good reproducibility, shorten the analysis time and reduce the size of the apparatus, it is indispensable that the separating column and detecting cell should be placed in the thermostatic oven that is used in the present invention. The material and shape of the thermostatic oven may be the same as those of an ordinary small thermostatic oven. Preferred thermostatic ovens are those in which temperature control of ±0.1° C. is possible within a range of 30° to 60° C. be used.

In the present invention, it is indispensible that a constant flow, pulse free pump capable of feeding a liquid at a constant rate with a pulsation of ±2% with changes of the pressure at a flow rate of 0.3 to 6 ml/min be used.

If the pulsation with changes of the pressure exceeds ±2%, the reproducibility of the time for elution of the components to be separated is poor, and a noise is generated which drastically reduces the quantitative determination sensitivity when low concentration components are detected. Various modifications have been made in known reciprocal piston-type delivery pumps, to eliminate pulsations with changes of the pressure. For example, cams differing in shape, or dampers have been used to absorb changes of the pressure. However, none of these proposals have proved satisfactory because pulsations are still too large.

As the constant flow pulse free feeding pump, there is preferably used a constant delivery device in which a signal of the pressure detected by a pressure detecting element arranged on the outlet of a flow passage is fed back to a micro-computer and according to the output of the computer corresponding to the pressure signal, the pressure reduced at the suction stroke of one quick return type pump is maintained at a predetermined level by increasing the rotation number of a stepping motor at the discharge stroke of the other quick return type pump. More specifically, there may preferably be adopted a constant flow, pulse free feeding pump which comprises a pressure detecting element arranged on the outlet of a flow passage, a micro-computer to which a signal of the pressure detected by the pressure detecting element is fed back and which controls the rotation number of a stepping motor of a quick return type pump according to the pressure signal thus fed back. The two quick return type pumps may be operated by the micro-computer.

According to the present invention, all the micro-concentration components present in an aqueous solution can be separated promptly and simultaneously with a good chromatographic reproducibility. The present invention includes the combined techniques of the de-ionization chromatography and ion exchange chromatography and the technique of the distribution chromatography.

As the micro-concentration components present in a sample aqueous solution which may be analyzed in accordance with the present invention, there can be mentioned components dissolved at a concentration of 0.01 to 5000 ppm, for example, inorganic anions, inorganic cations, complex ions, organic anions, organic cations, ampholytic ions, proteins, enzymes, nucleic acids and saccharides. According to the present invention, inorganic anions such as $Cl^-$, $Br^-$ and $I^-$, inorganic cations such as $NH_4^+$, $Na^+$ and $K^+$, complex ions such as $Fe(CN)_6^{4-}$ and $Fe(CN)_6^{3-}$, organic anions such as formates and acetates, organic cations such as trimethylamine and dimethylamine, and ampholytic ions such as amino acids, peptides, nucleic acid bases and nucleosides are separated especially advantageously.

In the present invention, eluting solutions capable of migrating a plurality of micro-concentration components present in a sample aqueous solution in the separating column can be used, and an eluting solution having a high affinity with an ion exchange gel and being capable of migrating ion seeds as the micro-concentration components bonded to the ion exchange gel are especially preferred. For example, in case of the anion exchange chromatography, there are preferably used eluting solutions capable of promoting elution of the anion seeds, for example, solutions of anion seeds, that is, such inorganic compounds as perchloric acid, sulfuric acid, bromic acid, nitrous acid, bicarbonate, dihydrogen phosphate and fluorine, and organic compounds such as tribasic acids, e.g., citric acid, isocitric acid and oxalosuccinic acid, dibasic acids, e.g., oxalic acid, succinic acid, malic acid, ketoglutaric acid and terephthalic acid, and monobasic acids, e.g., formic acid, acetic acid, pyruvic acid, lactic acid, glycolic acid and benzoic acid.

The counter-cation seed of the eluting solution to the anion seed is not particularly critical, but a cation not precipitating at a pH value of 2 to 13 and capable of being stably present at a concentration of $10^{-4}$ to $10^{-2}$M is preferred.

In the above-mentioned method of Small et al., since a deionizing column is used, an eluting solution containing a counter-cation seed forming a hydroxide cannot be used, but such limitation is not imposed in the present invention. This is one of characteristic features of the present invention.

In the case of the cation exchange chromatography, as the cation seed of the eluting solution capable of promoting elution of the cation seeds, there can be mentioned hydrogen ions and primary, secondary, tertiary and quaternary ammonium ions. These cation seed migrate the cation seeds bonded to a cation exchange gel. With cation exchange chromatography, in the case where the ion seed of the eluting solution forms, for example, a complex having a high affinity with the ion seed, it sometimes happens that the enhanced effect of migrating the cation seed from the ion exchange gel can be attained and better results can be obtained. As such eluting solution, there can be mentioned solutions of fluorine, ammonia, ethylene diamine, ethylene diamine tetraacetate, oxalic acid and tartaric acid.

In the present invention, an eluting solution of one compound may be used. However, in order to maintain a stable pH, an eluting solution of at least two compounds is preferably used. Moreover, a mixture of water and a water-soluble non-aqueous solvent may be used as the eluting solution. As the non-aqueous solvent, there are preferably used lower alcohols having 1 to 4 carbon atoms, carbonic acid esters, dioxane, tetrahydrofuran, or acetonitrile.

The counter-anion seed to the cation seed of the eluting solution is not particularly critical, but an anion not precipitatng at a pH value of 2 to 13 and being capable of being stably present at a concentration of $10^{-4}$ to $10^{-2}$M is preferred.

Embodiments of the present invention will now be described with reference to the accompanying drawings.

DETAILED DESCRIPTION OF THE PREFERRED EMBODIMENTS

Figure 1:
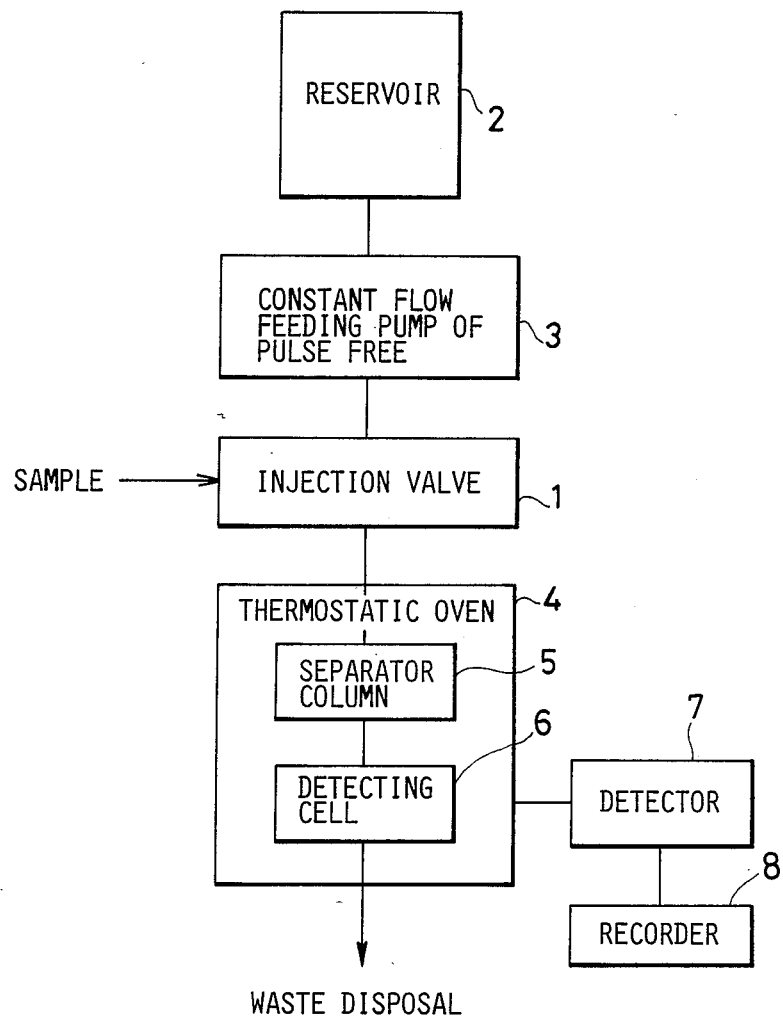
FIG. 1 is a flow diagram illustrating one embodiment of the present invention.

In FIG. 1, reference numeral 1 represents a sample injection valve of an introduction device, reference numeral 2 represents a reservoir of an eluting solution and reference numeral 3 represents a constant flow, pulse free feeding pump for feeding an eluting solution to the sample injection valve 1 from the eluting solution reservoir 2. A separating column 5 having a length of 20 to 90 mm and a detecting cell 6 for detecting eluates from the separating column 5 are arranged in the interior of a thermostatic oven 4. Reference numeral 7 represents an ordinary detector and reference numeral 8 represents a recorder connected to said detector 7.

Figure 4:
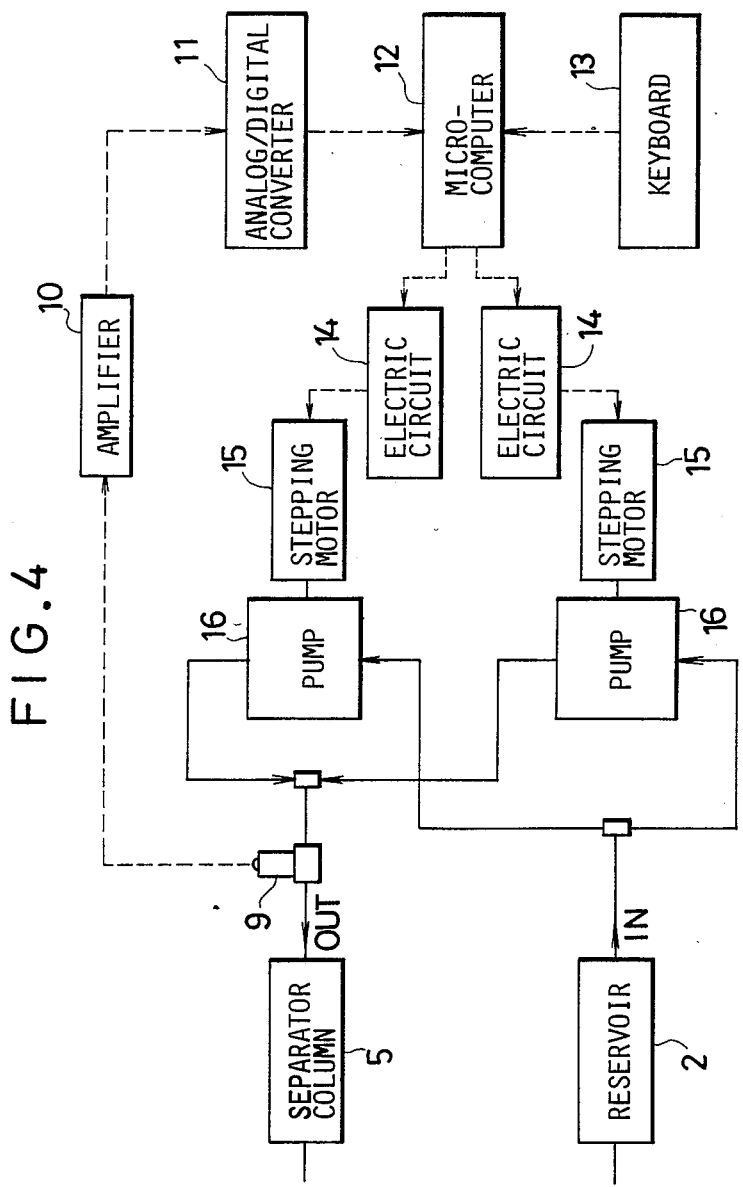
FIG. 4 is a schematic block diagram of system having a constant flow, pulse free feeding pump for carrying out the present invention.

The constant flow feeding pump (3), referring to FIG. 4, is arranged for the schematic block diagram for carrying out the present invention. In FIG. 4, reference numeral 9 represents a pressure detecting element, 10 an amplifier, 11 an analog/digital converter, 12 a microcomputer, 13 a keyboard, 14 an electric circuit, 15 a stepping motor and 16 a quick return type pump.

The analytic method of the present invention will now be described with reference to FIG. 1.

A predetermined amount of a sample aqueous solution containing a plurality of micro-concentration components is introduced into a system through the sample injection valve 1 by an eluting solution from the eluting solution reservoir 2 by the constant flow, pulse free feeding pump 3. A plurality of the micro-concentration components in the sample are separated by the separating column 5 arranged in the thermostatic oven 4, and the separated components are detected by the detecting cell 6 arranged in the thermostatic oven 4 and connected to the separating column 5. Variations of the concentrations in the detecting cell 6 are indicated by the detector 7 producing electric signals in proportion to the quantities of substances. Simultaneously, the electric signals produced by the detector 7 are supplied to the recorder 8 for displaying visible data corresponding to the electric signals. Thus, the analytic operation is completed.

The constant flow feeding pump is controlled at a predetermined pressure level by the following operation, in which a signal of the pressure detected by the pressure detecting element (9) arranged on the outlet of the flow passage of one quick return type pump (16) is fed back to the microcomputer (12) and according to the output of the computer corresponding to the pressure signal, the pressure reduced at the suction stroke of the quick return type pump (16) is maintained at predetermined pressure level by increasing the rotation number of the stepping motor (15) of another quick return type pump (16).

The present invention will now be described in detail with reference to the following Examples and Comparative Examples.

EXAMPLE 1

Constant flow, pulse free feeding pump: flow rate of 1.0 ml/min and pressure variation of $\pm 0.2$ Kg/cm$^2$ Separating column: stainless steel column having a length of 50 mm and an inner diameter of 4 mm and being packed with a trimethyl ammonium type anion exchange gel having a particle size of $5 \pm 1$ μm, a pore size of 2000 Å, an exchange capacity of 0.5 milliequivalent/g and a compression strength of at least 300 Kg/cm$^2$ Detecting cell: conductivity detecting cell having a cell capacity of 0.5 μl Thermostatic oven: oven having a size of 230 mm × 210 mm × 170 mm, in which the temperature is controlled to $40 \pm 0.1°$ C.

Figure 2:
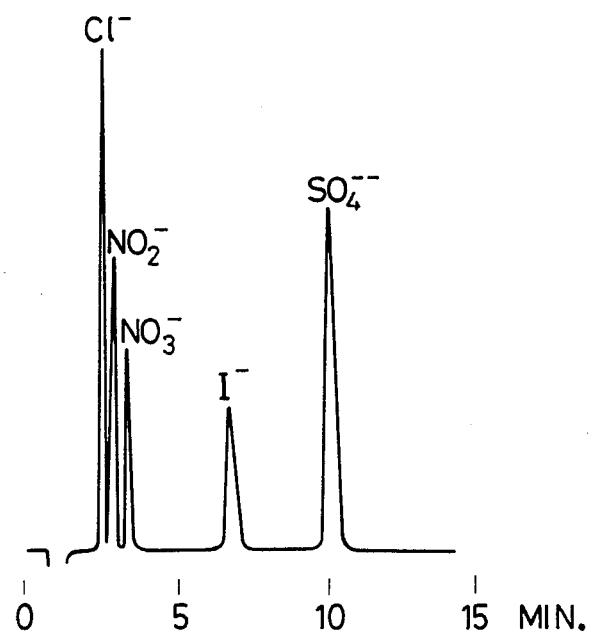
FIG. 2 is a chromatogram showing the state of separation of five anions.

By using the above-mentioned chromatographic analytic apparatus, micro-concentrations of chlorine, nitrous, nitric, iodine and sulfuric ions present in an aqueous solution were separated. The results obtained are shown in a chromatogram of FIG. 2. As is apparent from FIG. 2, the separation was completed within 12 minutes. In this analysis, each ion component was used in the form of a sodium or potassium salt and the concentration was adjusted to 5 ppm. An aqueous solution containing the foregoing ions (100 μl) was injected and an aqueous solution containing $5 \times 10^{-4}$M of diammonium citrate (pH value=5.2) was used as the eluting solution. The analysis was carried out at a flow rate of 1.0 ml/min under a pressure of 35 Kg/cm$^2$. The theoretical stage number indicating the column efficiency was 15,000 stages/m, and the detection limit of the nitric ion was 0.1 ppm. When the test was repeated 11 times, the reproducibility of the concentration and elution position varied less than $\pm 2\%$.

COMPARATIVE EXAMPLE 1

The operation was carried out in the same manner as described in Example 1 except that the detecting cell was not arranged in the thermostatic oven but the separating column alone was arranged in the thermostatic oven. When the test was repeated 11 times, the reproducibility of the concentration and elution position of the nitric ion varied more than $\pm 7\%$. The operation was carried out in the same manner as described in Example 1 except that the thermostatic oven was removed and the temperature of the atmosphere was changed within $\pm 5°$ C. When the test was repeated 11 times, the reproducibility of the concentration and elution position of the nitric ion again varied more than $\pm 7\%$.

COMPARATIVE EXAMPLE 2

The operation was carried out in the same manner as described in Example 1 except that a commercially available liquid feed pump (Model 396-89 supplied by Milton Roy Co.) was used. The pulsation due to the pressure change exceeded $\pm 2\%$, and the detection limit of the nitric ion was 1 ppm. When the test was repeated 11 times, the reproducibility of the concentration and elution position of the nitric ion varied more than than $\pm 5\%$.

COMPARATIVE EXAMPLE 3

Figure 3:
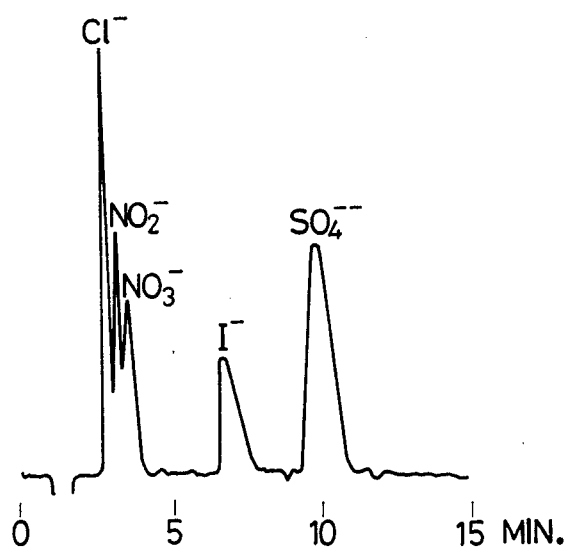
FIG. 3 is a chromatogram showing that if a large-capacity cell is employed, complete separation of nitrous and nitric ions is impossible

The operation was carried out in the same manner as described in Example 1 except that a commercially available conductivity detecting cell having a capacity of about 5 μl (supplied by Senshu Kagaku; the cell capacity being indicated as less than 10 μl) was used. The results obtained are shown in a chromatogram of FIG. 3. As is apparent from FIG. 3, the width of each peak was broader than in Example 1, and separation of the nitrous and nitric ions was especially incomplete.

EXAMPLE 2

Constant flow, pulse free feeding pump of pulse free: flow rate of 1.2 ml/min and pressure variation of 0.2 Kg/cm$^2$ Separating column: stainless steel column having a length of 40 mm and an inner diameter of 3 mm packed with a sulfonic acid type ion exchange gel having a particle size of 5±1 μm, a pore size of 2000 Å, an exchange capacity of 0.2 milliequivalent/g and a compression strength of at least 300 Kg/cm$^2$ Detecting cell: conductivity detecting cell having a cell capacity of 1.0 μl Thermostatic oven: oven having a size of 400 mm×130 mm×250 mm, in which the temperature is controlled to 45±1° C.

When an aqueous solution containing micro-concentrations of lithium, sodium, potassium, rubidium and cesium ions was analyzed using the above-mentioned chromatographic analytic apparatus, separation of the respective ions was completed within 10 minutes. Each ion was supplied in the form of a chloride and the concentration was adjusted to 2 ppm. An aqueous solution containing 1.2×10$^{-3}$M of nitric acid was used as the eluting solution and was fed at a flow rate of 1.2 ml/min under a pressure of 40 Kg/cm$^2$. When the test was repeated 11 times, the reproducibility of the concentration and elution position of the potassium ion varied less than ±2%, and the detection limit of the potassium ion was 0.05 ppm.

COMPARATIVE EXAMPLE 4

The operation was carried out in the same manner as described in Example 2 except that a commercially available, ion exchange gel-packed, large-size cylindrical column (stainless steel column having a length of 340 mm and an inner diameter of 2 mm packed with a cation exchange gel, Uydac SC supplied by Separations Group Co.) was used and the flow rate of the constant flow feeding pump was changed to 0.7 ml/min. Elution of all the ions was completed within about 15 minutes, but separation of lithium and sodium was incomplete.

We claim:

1. A chromatographic analytical apparatus comprising:
   1. A column from 20 to 90 mm in length for separation of the components of an aqueous sample solution, said column containing a spherical porous barrier comprising an ion exchange gel having particle size of 1 to 8 μm, a pore size less than 1000 Å, an ion exchange capacity of 0.03 to 1.0 milliequivalents/g and a mechanical strength greater than 200 kg/cm$^2$,
   2. a detecting cell having a cell capacity less than 1.9 μl for detecting eluates from the separating column,
   3. a detector operatively connected to the detecting cell, and
   4. a constant flow, pulse free feeding pump for feeding an eluting solution to the separating column, said column, detector and pump being operatively connected, said separating column and detecting cell arranged in a thermostatic oven.

* * * * *